United States Patent
Liu et al.

(10) Patent No.: US 9,362,627 B2
(45) Date of Patent: Jun. 7, 2016

(54) ARTIFICIAL MICROSTRUCTURE AND ARTIFICIAL ELECTROMAGNETIC MATERIAL USING THE SAME

(71) Applicants: Kuang-Chi Institute of Advanced Technology, Shenzhen (CN); Kuang-Chi Innovative Technology Ltd., Shenzhen (CN)

(72) Inventors: Ruopeng Liu, Shenzhen (CN); Lin Luan, Shenzhen (CN); Chaofeng Kou, Shenzhen (CN); Jincai Ye, Shenzhen (CN)

(73) Assignees: Kuang-Chi Innovative Technology Ltd., Shenzhen (CN); Kuang-Chi Institute of Advanced Technology, Shenzhen, Guangdong (CN)

( * ) Notice: Subject to any disclaimer, the term of this patent is extended or adjusted under 35 U.S.C. 154(b) by 0 days.

(21) Appl. No.: 14/844,195

(22) Filed: Sep. 3, 2015

(65) Prior Publication Data

US 2015/0380830 A1     Dec. 31, 2015

Related U.S. Application Data

(62) Division of application No. 13/577,534, filed as application No. PCT/CN2011/081370 on Oct. 27, 2011.

(30) Foreign Application Priority Data

Jul. 29, 2011    (CN) .......................... 2011 1 0216571

(51) Int. Cl.
*H01Q 17/00*    (2006.01)
*A61N 1/16*     (2006.01)
*H05K 9/00*     (2006.01)
*H01Q 15/00*    (2006.01)

(52) U.S. Cl.
CPC ............... *H01Q 17/008* (2013.01); *A61N 1/16* (2013.01); *H01Q 15/0086* (2013.01); *H05K 9/0081* (2013.01); *G02F 2202/30* (2013.01)

(58) Field of Classification Search
CPC ...................... H01Q 15/0026; H01Q 15/0086
See application file for complete search history.

(56) References Cited

U.S. PATENT DOCUMENTS

| 7,218,090 | B1 * | 5/2007 | Nalbandian | G01R 29/0878 324/633 |
|---|---|---|---|---|
| 7,683,444 | B2 * | 3/2010 | Tonucci | G02F 1/015 250/336.1 |
| 8,120,546 | B2 * | 2/2012 | Smith | H01Q 15/02 343/909 |
| 8,556,178 | B2 * | 10/2013 | Wang | H01Q 1/2216 235/439 |
| 2009/0310926 | A1 * | 12/2009 | D'Aguanno | B82Y 20/00 385/129 |

(Continued)

FOREIGN PATENT DOCUMENTS

CN          101976759 B  *  4/2013

*Primary Examiner* — Matthew M Barker
(74) *Attorney, Agent, or Firm* — Young Basile Hanlon & MacFarlane, P.C.

(57) ABSTRACT

The present invention provides an artificial microstructure. The artificial microstructure includes at least three split rings. The at least three split rings surround and embed in turn. Each split ring is formed by a wire which is made of conductive material, with two terminals of the wire towards each other to form an opening of the corresponding split ring. The present invention also provides an artificial electromagnetic material using the artificial microstructure. The artificial electromagnetic material with the artificial microstructure can achieve the function of broadband wave-absorbing.

18 Claims, 6 Drawing Sheets

(56) References Cited

U.S. PATENT DOCUMENTS

2010/0053019 A1* 3/2010 Ikawa .................... H01Q 9/285
　　　　　　　　　　　　　　　　　　　　　343/866

2011/0152725 A1* 6/2011 Demir .................. A61B 5/0031
　　　　　　　　　　　　　　　　　　　　　600/587

2012/0057616 A1* 3/2012 Padilla .................. G01J 3/2803
　　　　　　　　　　　　　　　　　　　　　374/179

* cited by examiner

PRIOR ART

ARTIFICIAL MICROSTRUCTURE AND ARTIFICIAL ELECTROMAGNETIC MATERIAL USING THE SAME

CROSS REFERENCE TO RELATED APPLICATIONS

This application is a divisional application of a commonly-assigned application entitled "ARTIFICIAL MICROSTRUCTURE AND ARTIFICIAL ELECTROMAGNETIC MATERIAL USING THE SAME", filed on Aug. 7, 2012 with application Ser. No. 13/577,534. The disclosure of the above-identified application is incorporated herein by reference.

FIELD OF THE INVENTION

The present invention relates to electromagnetic field, and particularly, to an artificial microstructure and an artificial electromagnetic material using the same.

BACKGROUND OF THE INVENTION

With the development of modern science and technology, the effects of electromagnetic radiation on the environment are becoming increasingly serious. At the airport, aircrafts could not take off due to electromagnetic interference and are delayed. In the hospital, a plurality of electronic diagnosis and treatment apparatuses cannot work properly due to interferences of mobile phones. Therefore, controlling electromagnetic pollution and searching for a kind of wave-absorbing material for resisting and weakening electromagnetic radiation have become a major issue in material science.

Wave-absorbing material can effectively absorb incident electromagnetic waves and make incident electromagnetic waves be scattered and attenuated. Wave-absorbing material can convert the incident electromagnetic wave into heat or other forms of energy through various loss mechanisms of the material for the purpose of absorbing wave. Wave-absorbing material includes structural wave-absorbing material and coated wave-absorbing material. The former mainly is wedge-shaped, bubble-shaped, flat-shaped and etc. The latter is compounded by binder and absorbent, the absorbing ability is mostly related to the type of the absorbent. However, each type of the wave-absorbing material has a constant absorbing frequency band which cannot be changed freely.

A new synthetic material, called artificial electromagnetic material (metamaterial), has a feature that it can be designed freely according to different working frequency band, and therefore comes to be a new direction in the study of wave-absorbing material.

Figure 1:
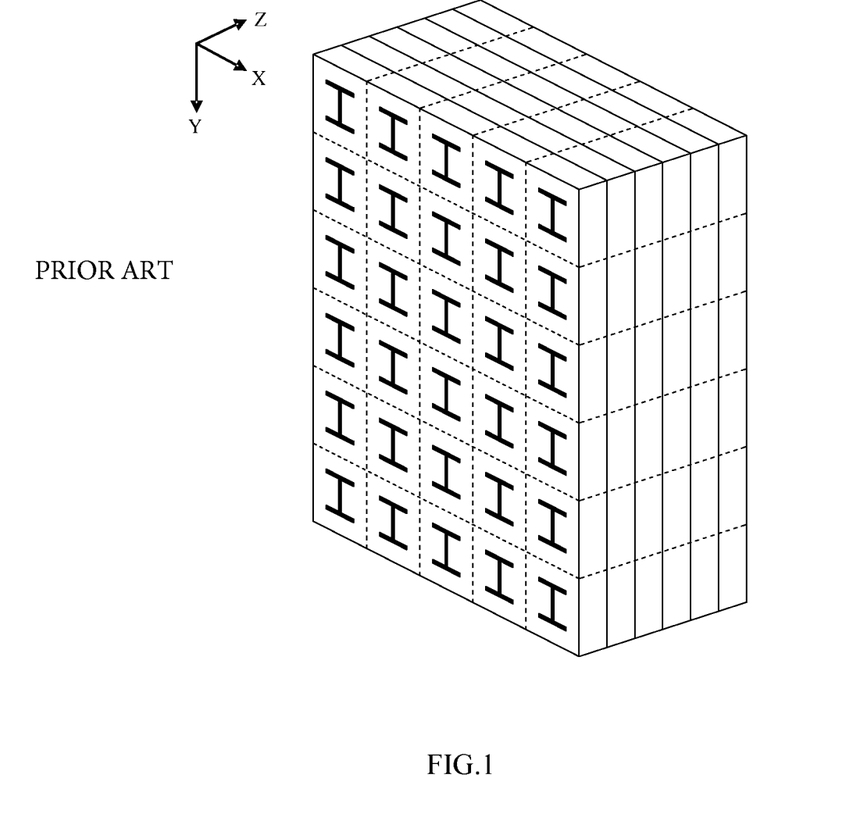
FIG. 1 is a schematic diagram of an embodiment of a conventional artificial electromagnetic material.

The artificial electromagnetic material is new synthetic material which can respond to electromagnetic waves. Referring to FIG. 1, the artificial electromagnetic material includes a substrate and a plurality of artificial microstructures attached to the substrate. Since the artificial microstructures usually have a certain shape such as "I" shape constructed by metal wires, the microstructures can respond to electromagnetic waves, thereby the artificial electromagnetic material reflects different electromagnetic properties from that of the substrate. Designing artificial microstructures with special properties, a broadband wave-absorbing material can be achieved. And if sizes and shape of the artificial microstructures are changed, the absorbing band of the artificial electromagnetic material will be changed.

DISCLOSURE OF THE INVENTION

Aiming at the defect that the existing wave-absorbing material has constant absorbing frequency band, a technical problem to be solved in present invention is to provide an artificial microstructure and an artificial electromagnetic material using the same which can absorb wave in a broad frequency band while their absorbing band can be designed.

The present invention provides an artificial microstructure which includes at least three split rings, wherein the at least three split rings surround and embed in turn, each split ring is formed by a wire which is made of conductive material, with two terminals of the wire towards each other to form an opening of the corresponding split ring.

The split rings are circular split rings, the at least three split rings are arranged concentrically.

A center angle between the openings of the two adjacent circular split rings relative to the center of the circle is 180 degrees.

The split ring is a rectangle.

The split ring is a triangle.

The at least three split rings are geometrically similar, and the corresponding sides of the at least three split rings are parallel.

The openings of two adjacent split rings are defined away from each other.

The artificial microstructure is made of metal.

The artificial microstructure is made of silver or copper.

The artificial microstructure is made of copper alloy.

The artificial microstructure is made of nonmetal material.

The artificial microstructure is made of conductive plastic.

The present invention further provides an artificial electromagnetic material. The artificial electromagnetic material includes at least one material sheet. Each material sheet includes a substrate and a plurality of above-mentioned artificial microstructures attached to the front surface of the substrate; a metal foil is attached to the back surface of the substrate.

The substrate includes a plurality of rectangle substrate units which are the same and arranged at array along the surface of the substrate, with each one's front surface attached with one artificial microstructure and back surface attached with one metal foil unit while the metal foil includes a number of the metal foil units.

The metal foil units cover the whole back surface of the corresponding substrate unit except for four corners of the corresponding substrate unit.

The plurality of artificial microstructures are the same, and the plurality of metal foil units are the same.

The substrate includes a plurality of rectangle substrate units which are the same and arranged at array along the surface of the substrate, with each one's front surface attached with one artificial microstructure, the metal foil is a fishnet structure, meshes of the fishnet structure are located on the common junction of the four adjacent substrate units.

The substrate is made of polyfluortetraethylene or epoxide resin.

There are several material sheets, which are arranged along a direction perpendicular to the substrate, set parallelly and spaced evenly.

The row spacing and the column spacing of the artificial microstructure array are either smaller than or equal to one tenth of the wavelength of the incident electromagnetic wave absorbed by the artificial electromagnetic material.

The present invention of artificial electromagnetic material, which can achieve the broadband wave-absorbing, have the following beneficial effects: owing to the front surface of the substrate attached with the artificial microstructures, which includes a plurality of split rings, and the back surface of the substrate attached with the metal foil, electromagnetic waves will reflected by the metal foil to re-enter the substrate after passing through the artificial microstructure. The electromagnetic waves are absorbed repeatedly. Therefore, the artificial electromagnetic material can achieve broadband wave-absorbing in high efficiency.

Other advantages and novel features of the present disclosure will become more apparent from the following detailed description of preferred embodiment when taken in conjunction with the accompanying drawings.

DETAILED DESCRIPTION OF ILLUSTRATED EMBODIMENTS

Figure 2:
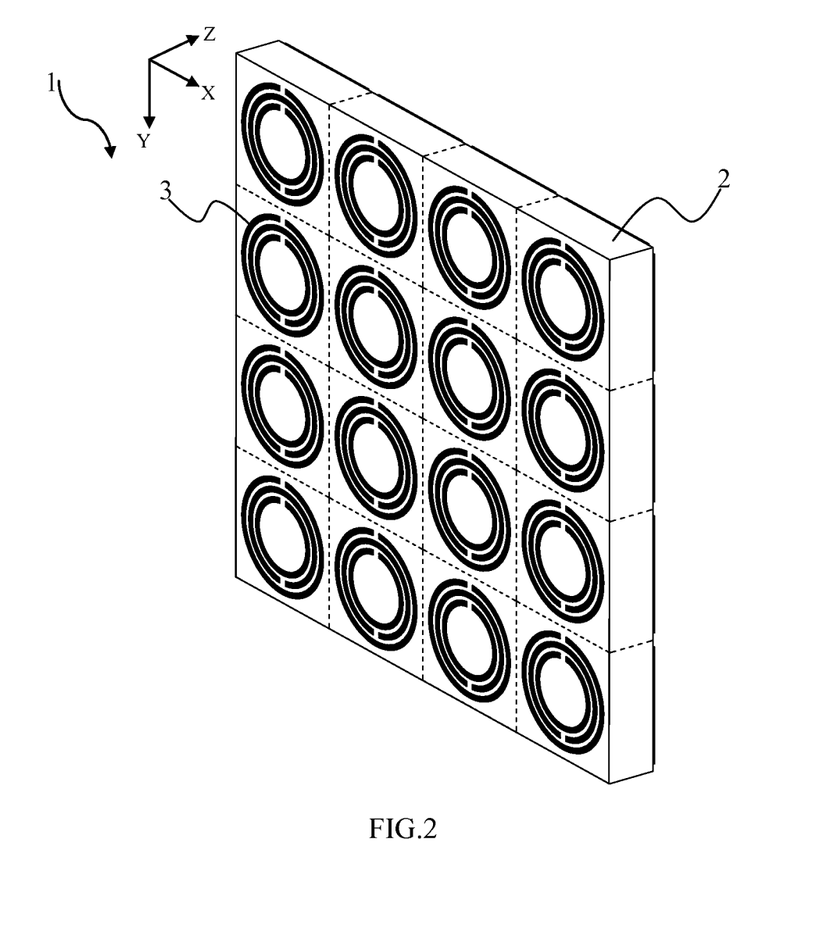
FIG. 2 is a front view of an artificial electromagnetic material according to a first embodiment.
Figure 3:
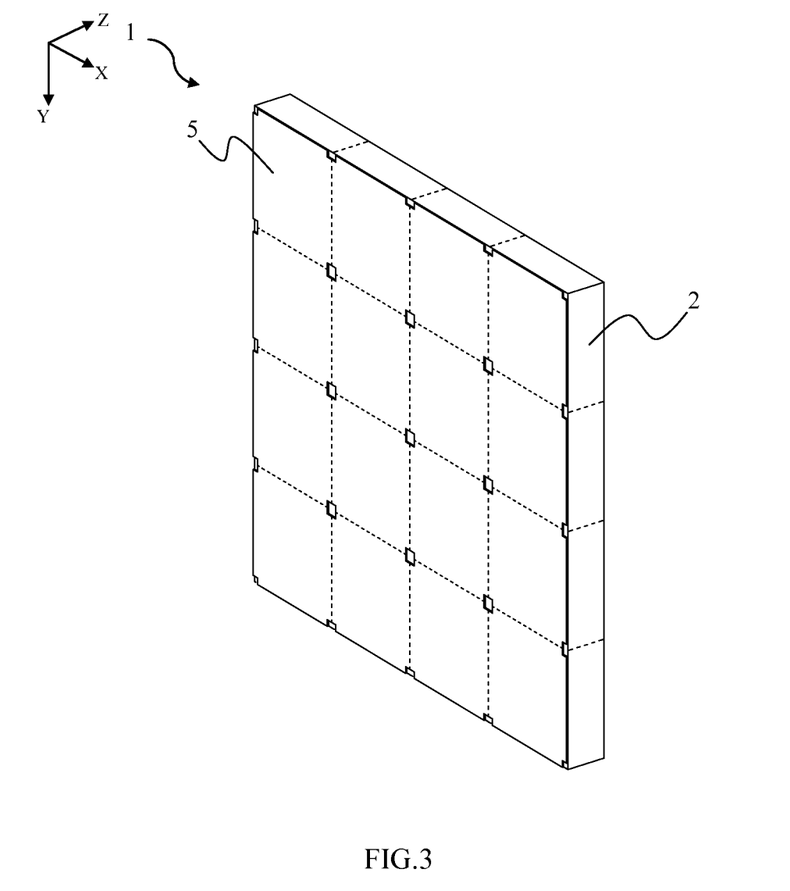
FIG. 3 is a back view of the artificial electromagnetic material of FIG. 2.

Referring to FIGS. 2 and 3, the present invention relates to an artificial electromagnetic material for broadband wave-absorbing. The artificial electromagnetic material includes at least one material sheet 1. Each material sheet 1 includes a substrate 2 and a plurality of artificial microstructures 3 attached to a surface of the substrate 1. The plurality of artificial microstructures 3 are periodically arranged on the surface of the substrate 2, such as arranged in rectangular array. In the rectangular arrays, X direction is defined as the direction of rows, Y direction perpendicular to X direction is defined as the direction of columns. In the rectangular array, the row spacings are the same and the column spacings are the same. Even the row spacing and the column spacing are equal. Preferably, the row spacing and the column spacing are not greater than one fifth of the wavelength of the absorbed incident electromagnetic wave. Preferably, the row spacing and the column spacing are equal to one tenth of the wavelength of the absorbed incident electromagnetic wave. If there are several material sheets 1, the material sheets 1 are arranged along Z direction perpendicular to the substrate 2 in turn. The material sheets 1 are set parallelly. Preferably, the material sheets 1 are parallel and spaced evenly.

In the invention of the artificial electromagnetic material, the artificial microstructure 3 is attached to a front surface of the substrate 2. Metal foil 5 is attached to a back surface of the substrate 2. The thickness of the metal foil 5 is substantially in a range of 0.018-0.035 mm. The metal foil 5 is usually made of copper or silver. The metal foil 5 can reflect the electromagnetic wave transmitted into the substrate 2 to make the electromagnetic wave re-enter the substrate 2. The substrate 2 absorbs the re-entered electromagnetic wave. The times of the electromagnetic wave entering the substrate 2 increases, which results in the electromagnetic wave are repeatedly absorbed. Therefore, the ability of absorbing waves is improved.

The metal foil 5 can be as a whole slice of foil film which is attached to the back surface of the substrate 2. Preferably, the metal foil 5 is fish net shaped, that is, a plurality of meshes are evenly defined in the whole slice of foil film. The plurality of meshes are located on the common junction of the four adjacent substrate units.

Figure 4:
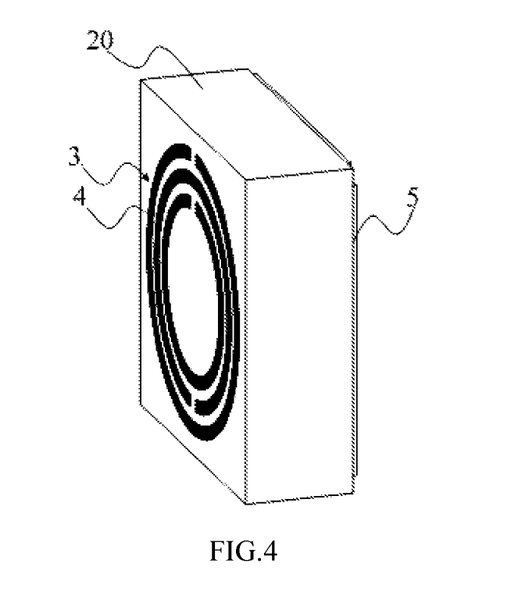
FIG. 4 is a front view of a material unit of the artificial electromagnetic material of FIG. 2.
Figure 5:
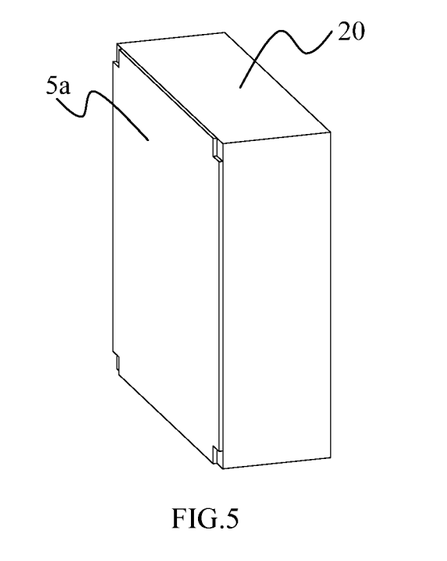
FIG. 5 is a back view of the material unit of FIG. 4.

Referring to FIGS. 4 and 5, the artificial microstructure 3 is arranged in an array, so the substrate 2 can be virtually divided into a number of substrate units 20 arranged in the same array. The length of each substrate unit 20 is equal to the above-mentioned row spacing. The width of each substrate unit 20 is equal to the above-mentioned column spacing. The thickness of each substrate unit 20 is equal to the thickness of the substrate 2. Surface of each substrate unit 20 just corresponds to one artificial microstructure 3.

Metal foil 5 is virtually divided into a plurality of metal foil units 5a according to the same division rule of the metal unit. The metal foil units 5a are arranged in multiple arrays, in which X direction is defined as the direction of the line, and Y direction is defined as the direction of the row. Referring to FIG. 5, each metal foil unit 5a covers the whole back surface of the corresponding substrate unit 20 except for four corners of the back surface of the corresponding substrate unit 20. One mesh is formed by one corner and the corners of the adjacent three metal foil units 5a together (see FIG. 3). Preferably, each artificial microstructure 3 is the same and each metal foil unit 5a is the same. That achieves the uniform absorption effect on any positions of the substrate 2.

The metal foil 5 with the meshes is applied to make the electromagnetic waves passing through the meshes produce electromagnetic effects, to further cause the accumulation of quantity of electron. Therefore, capacitive effect between the metal foil 5 and former structure is enhanced. The metal foil 5 has a great reflection effect for the electromagnetic waves, Therefore, the transmission distance of the electromagnetic waves in the substrate 2 increases and the wave-absorbing effect also increases.

The advantages of the present invention are that the shape of the artificial microstructure 3 is a new geometry pattern. The artificial microstructure 3 includes at least three split rings 4. The at least three split rings 4 surround and embed in turn. That is, a second split ring is located in a first split ring. A third split ring is located in the second split ring, and the rest of the split rings can be located in the same manner. Each split ring is formed by a wire which is made of conductive material, with two terminals of the wire towards each other to form an opening of the corresponding split ring. The conductive material can be metal material, such as silver, copper, copper alloy, and so on. The conductive material also can be non-metal material such as conductive plastic, and so on. The at least three split rings 4 which are surrounded and embedded in turn can realize the function of broadband wave-absorbing.

FIG. 4 is a schematic diagram of the first embodiment of the artificial microstructure. The artificial microstructure includes three split rings 4. Each split ring 4 is a circular split ring. That is, the split ring, formed by a wire with the two terminals of the wire are connected together, is circular ring. Preferably, each circular split ring is arranged concentrically. That is, every circular split ring 4 has the same centre of a circle, and the centre angle between the openings of the two adjacent circular split rings 4 related to the centre of the circle is equal to 180 degrees.

Figure 6:
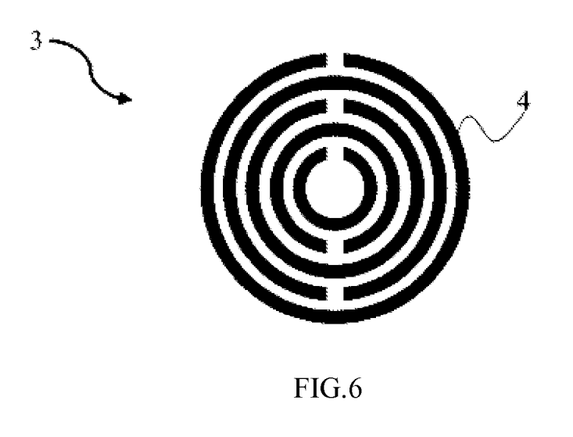
FIG. 6 is a schematic diagram of an artificial microstructure according to a second embodiment.

FIG. 6 is a schematic diagram of an artificial microstructure of the second embodiment, and similar to the artificial microstructure of the first embodiment. A difference between the second embodiment and the first embodiment of the artificial microstructure is the number of the split rings 4. In the second embodiment, the number of the split rings 4 is five.

Figure 7:
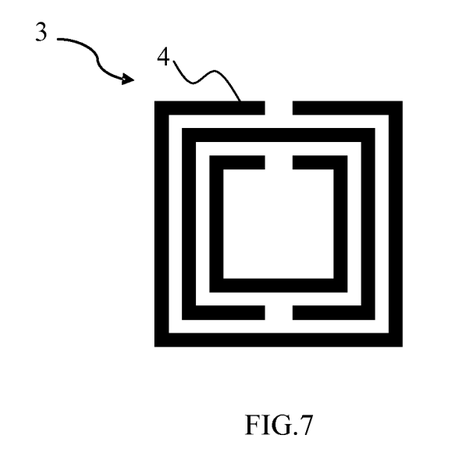
FIG. 7 is a schematic diagram of an artificial microstructure according to a third embodiment.
Figure 8:
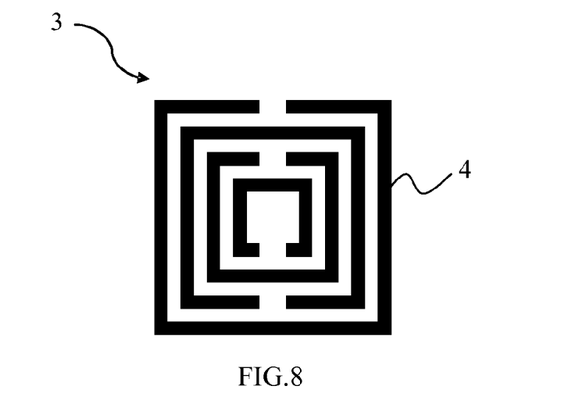
FIG. 8 is a schematic diagram of an artificial microstructure according to a fourth embodiment.

Similarly, FIG. 7 is a schematic diagram of an artificial microstructure of the third embodiment. FIG. 8 is a schematic diagram of an artificial microstructure of the fourth embodiment. A difference among the third, fourth embodiments, and the first embodiment is the shape of the split ring 4 of the artificial microstructure 3. In the third and fourth embodiments, the split ring 4 is a rectangle. Sides of the split rings 4 are parallel correspondingly. In the third embodiment, the number of the split rings 4 is three. In the fourth embodiment, the number of the split rings 4 is four. Preferably, the openings of the two adjacent split rings 4 are defined away from each other, That is, the opening of one of the two adjacent split rings 4 is defined in a rectangle side. The opening of the other of the adjacent two split rings 4 is defined in a rectangle side parallel to the rectangle side of the former split ring 4.

Figure 9:
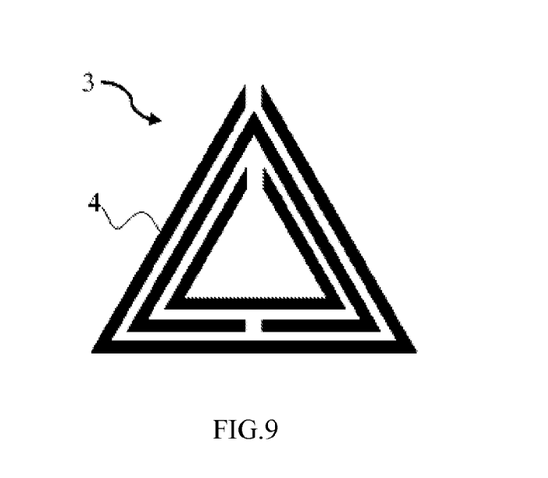
FIG. 9 is a schematic diagram of an artificial microstructure according to a fifth embodiment.
Figure 10:
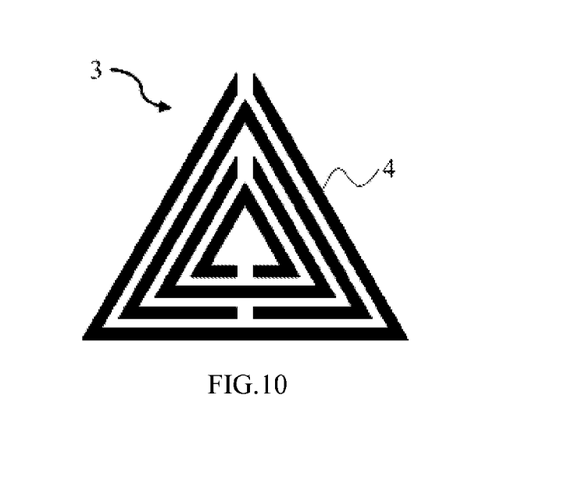
FIG. 10 is a schematic diagram of an artificial microstructure according to a sixth embodiment.

Similarly, FIG. 9 is a schematic diagram of the artificial microstructure of the fifth embodiment. FIG. 10 is a schematic diagram of the artificial microstructure of the sixth embodiment. A difference among the fifth, sixth embodiments, and the first embodiment is the shape of the split rings 4. In the fifth and sixth embodiment, the split ring 4 is a triangle. In the fifth embodiment, the number of the triangle split rings 4 is three. In the sixth embodiment, the number of the triangle split rings 4 is four. Preferably, the openings of the two adjacent split rings 4 face to each other. That is, the opening of one of the two adjacent split rings 4 is defined in a vertex angle of the split ring 4. The opening of the other of the two adjacent split rings 4 is defined in a bottom opposite to the vertex angle of the split ring 4.

The shapes of the at least three split rings 4 of the artificial microstructure 3 are not limited to only satisfy the above described three shapes. The shapes of the at least three split rings 4 of the artificial microstructure 3 can be other arbitrary shapes. The at least three split rings 4 of the artificial microstructure 3 are not necessary the same shapes or geometrically similar. The at least three split rings 4 of the artificial microstructure 3 can be a mixture of the above described all kinds of the split rings 4, or a mixture of other split rings of irregular shape.

Artificial electromagnetic material of the present invention has the effect of broadband wave-absorbing. For example, in the first embodiment, the substrate 2 is made of FR-4 epoxy resin material. The size of the substrate unit 20 is 6 mm.times.6 mm.times.0.4 mm, wherein 0.4 mm is the thickness of the substrate 2. The outer diameter of the three split rings 4 are respectively 5.9 mm, 5.6 mm, and 5.3 mm. The wire of the split rings 4 is made of copper. The width of the wire is substantially 0.2 mm. The thickness of the wire is substantially 0.018 mm. The metal foil unit 5 is copper foil. The thickness of the copper foil is substantially 0.018 mm. Each of the uncoated Areas located in the four corners is substantially 0.1 mm.times.0.1 mm.

After simulation on above-mentioned artificial electromagnetic material formed by the substrate units, the artificial electromagnetic material can absorb at least 80% of the electromagnetic wave of which the frequency range is from 15.05 GHz to 15.42 GHz. Therefore, the above-mentioned embodiment of the artificial electromagnetic material has a great effect for absorbing electromagnetic wave of which the frequency range is from 15.05 GHz to 15.42 GHz., to achieve broadband wave-absorbing.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention.

What is claimed is:

1. An artificial electromagnetic material comprising:
   at least one material sheet comprising:
      a substrate comprising a front surface and a back surface; and
      a plurality of artificial microstructures attached on the front surface of the substrate;
   wherein a metal foil is attached to the back surface of the substrate;
   wherein each artificial microstructure comprises at least three split rings, the at least three split rings surround and embed in turn, each split ring is formed by a wire which is made of conductive material, with two terminals of the wire towards each other to form an opening of the corresponding split ring;
   wherein the substrate comprises a plurality of rectangular substrate units that are identical and arranged in an array to form the front surface and the back surface, a front surface of each rectangular substrate unit attached with one artificial microstructure; and
   wherein the metal foil has a fishnet structure, each mesh of the fishnet structure located on a common junction of four adjacent rectangular substrate units.

2. The artificial electromagnetic material of claim 1, wherein the metal foil comprises a plurality of metal foil units, a back surface of each rectangular substrate unit attached with one metal foil unit.

3. The artificial electromagnetic material of claim 2, wherein the plurality of artificial microstructures are the same, and the plurality of metal foil units are the same.

4. The artificial electromagnetic material of claim 2, wherein each metal foil unit covers an entirety of the back surface of a corresponding rectangular substrate unit except for four corners of the corresponding rectangular substrate unit, and one mesh is formed by one corner of one metal foil unit and corners of three metal foil units adjacent to the one metal foil unit.

5. The artificial electromagnetic material of claim 1, wherein the substrate is made of polyfluortetraethylene or epoxide resin.

6. The artificial electromagnetic material of claim 1, further comprising:
   a plurality of material sheets, which are arranged along a direction perpendicular to the substrate, set in parallel and spaced evenly.

7. The artificial electromagnetic material of claim 1, wherein a row spacing and a column spacing of an array formed by the plurality of artificial microstructures are either smaller than or equal to one tenth of a wavelength of an incident electromagnetic wave absorbed by the artificial electromagnetic material.

8. The artificial electromagnetic material of claim 1, wherein each split ring of the at least three split rings is a circular split ring, and the at least three split rings are arranged concentrically.

9. The artificial electromagnetic material of claim 8, wherein a center angle between the openings of two adjacent split rings relative to a center about which the at least three split rings are arranged is 180 degrees.

10. The artificial electromagnetic material of claim 1, wherein each split ring of the at least three split rings is a rectangular split ring.

11. The artificial electromagnetic material of claim 1, wherein each split ring of the at least three split rings is a triangular split ring.

12. The artificial electromagnetic material of claim 1, wherein the openings of two adjacent split rings are defined away from each other.

13. The artificial electromagnetic material of claim 1, wherein each artificial microstructure is made of metal.

14. The artificial electromagnetic material of claim 1, wherein each artificial microstructure is made of silver, copper or a copper alloy.

15. The artificial electromagnetic material of claim 1, wherein each artificial microstructure is made of nonmetal material.

16. The artificial electromagnetic material of claim 1, wherein each artificial microstructure is made of conductive plastic.

17. The artificial electromagnetic material of claim 1, wherein a width and a thickness of each split ring are substantially equal.

18. An artificial electromagnetic material comprising:
    at least one material sheet comprising:
        a substrate comprising a front surface and a back surface; and
        a plurality of artificial microstructures attached on the front surface of the substrate;
    wherein a metal foil is attached to the back surface of the substrate;
    wherein each artificial microstructure comprises at least three split rings, the at least three split rings surround and embed in turn, each split ring is formed by a wire which is made of conductive material, with two terminals of the wire towards each other to form an opening of the corresponding split ring,
    wherein the substrate comprises a plurality of rectangular substrate units that are identical and arranged in an array to form the front surface and the back surface, a front surface of each rectangular substrate unit attached with one artificial microstructure and a back surface of each rectangular substrate unit attached with one metal foil unit while the metal foil comprises a plurality of the metal foil units, and
    wherein each metal foil unit covers the whole back surface of the corresponding rectangular substrate unit except for four corners of the corresponding rectangular substrate unit.

* * * * *